(12) United States Patent
Harada et al.

(10) Patent No.: US 7,508,904 B2
(45) Date of Patent: Mar. 24, 2009

(54) X-RAY CT APPARATUS

(75) Inventors: Tomokazu Harada, Tochigi-ken (JP);
Makoto Nakano, Tochigi-ken (JP);
Tetsuya Sadotomo, Tochigi-ken (JP);
Yasutaka Shindo, Tochigi-ken (JP);
Katsumi Gotanda, Tochigi-ken (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/748,274

(22) Filed: May 14, 2007

(65) Prior Publication Data

US 2007/0274436 A1 Nov. 29, 2007

(30) Foreign Application Priority Data

May 12, 2006 (JP) ............................. 2006-133817

(51) Int. Cl.
*G01N 23/00* (2006.01)
(52) U.S. Cl. ........................... 378/15; 378/193; 378/197
(58) Field of Classification Search ..................... 378/4, 378/15, 193, 197
See application file for complete search history.

(56) References Cited

U.S. PATENT DOCUMENTS 6,337,894 B1 * 1/2002 Tybinkowski et al. .......... 378/4

7,010,081 B2 3/2006 Brunnett et al.
2007/0274436 A1 11/2007 Harada et al.

FOREIGN PATENT DOCUMENTS

JP 8-10250 1/1996
JP 2002-172112 6/2002

OTHER PUBLICATIONS

U.S. Appl. No. 11/964,508, filed Dec. 26, 2007, Sadotomo et al.

* cited by examiner

*Primary Examiner*—Jurie Yun
(74) *Attorney, Agent, or Firm*—Oblon, Spivak, McClelland, Maier & Neustadt, P.C.

(57) ABSTRACT

An X-ray CT apparatus, wherein a drum type rotation frame is rotatably supported by a fixed circular frame so as to surround an outer surface of the drum type rotation frame through a plurality of bearings provided between an inner surface of the fixing circular frame and an outer surface of the drum type rotation frame, for example in ring-like configuration. When the drum type rotation frame receives a large centrifugal acceleration due to a high speed rotation, outside expansion of the drum type rotation frame can be constrained due to both the rigidity of the fixed frame and the rigidity of the plurality of bearings provided on the outer surface of the rotation frame, thereby to maintain the relative positions of the X-ray tube and the X-ray detector and prevent deterioration of reconstructed images.

24 Claims, 8 Drawing Sheets

BACKGROUND
FIG. 7B

BACKGROUND
FIG. 7A

BACKGROUND

FIG. 8

X-RAY CT APPARATUS

CROSS-REFERENCE TO RELATED APPLICATIONS

This application claims priority from, and the benefit of, Japanese Patent Application No. 2006-133817, filed on May 12, 2006, the contents of which are expressly incorporated herein by reference in their entirety.

BACKGROUND OF THE INVENTION

1. Field of the Invention

The present invention relates to an X-ray computer tomography (CT) apparatus, and particularly, to an X-ray CT apparatus that can prevent displacements of an X-ray source and an X-ray detector that are mounted on a rotation frame provided in a gantry of the X-ray CT apparatus when the rotation frame rotates at high speed.

2. Discussion of the Background

Figure 8:
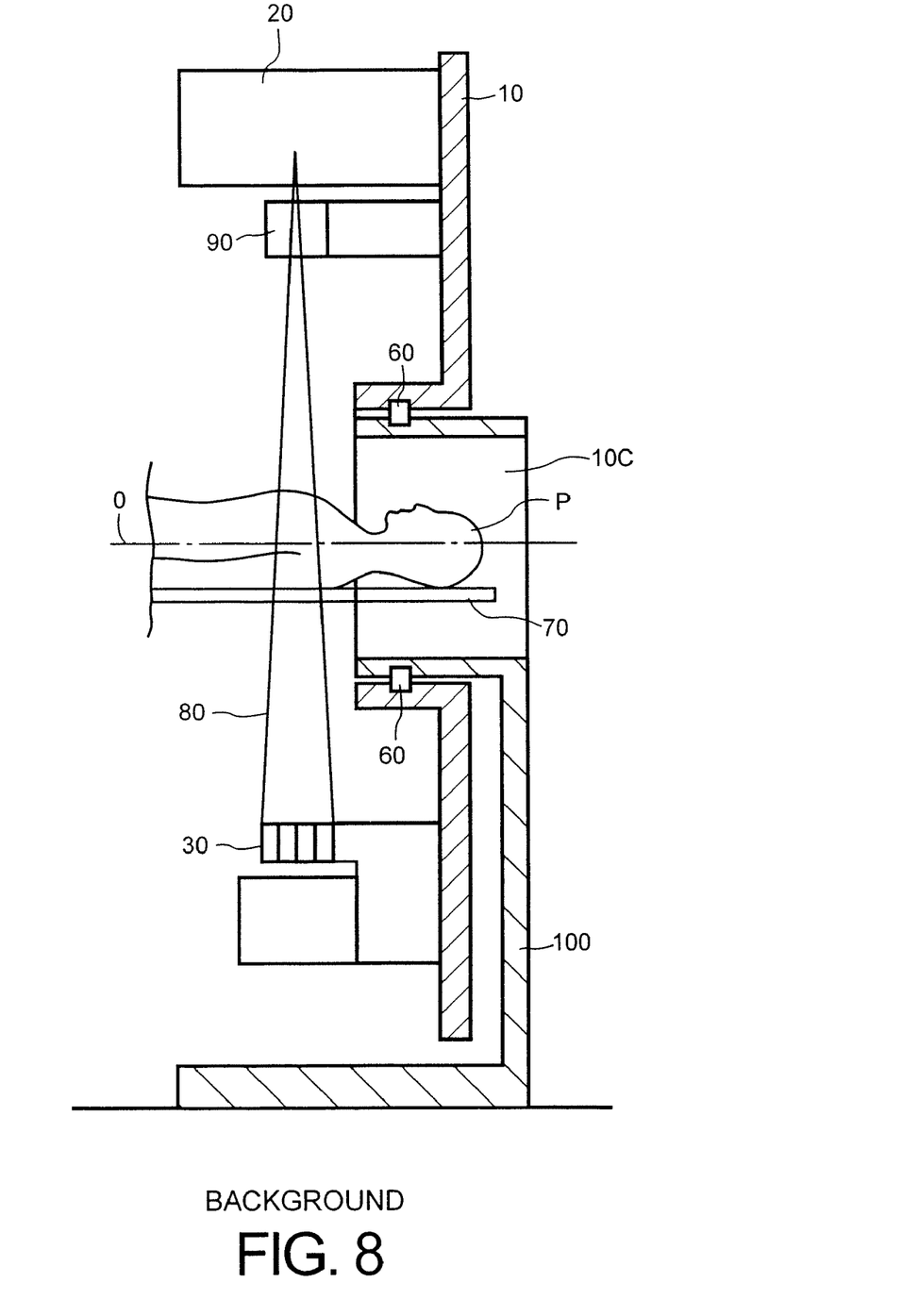
FIG. 8 is a cross-sectional view of a gantry portion of an X-ray CT apparatus provided to explain a background of a rotation frame supporting configuration.

Usually, an X-ray CT apparatus includes, as illustrated in FIG. 8, an X-ray tube 20 and an X-ray detector 30 provided on a vertical circle member of a rotation frame 10 in a gantry so as to face each other through a center aperture 10C of the gantry. An object P is inserted into the center aperture 10C of the gantry. A horizontal drum member of the rotation frame 10 is rotatably supported by a fixing base 100 fixed on a floor. Thus, a plurality of bearings 60 is provided between an outer surface of the drum member of the rotation frame 10 and a horizontal drum member of the fixing base 100. Consequently, X-ray tube 20 and X-ray detector 30 provided on the rotation frame 10 face each other through the aperture 10C are continuously rotated around an objected inserted into the center aperture 10C of the gantry while supported on a top plate 70. X-ray beams irradiated from the X-ray tube 20 through a diaphragm mechanism 90 penetrate the object P and are detected by the X-ray detector 30 as a plurality of X-ray projection data. On the rotation frame 10, other devices, such as a high voltage generation apparatus for supplying a high voltage to the X-ray tube 20 and a cooling apparatus for cooling the apparatus, are also mounted.

Figure 7A:
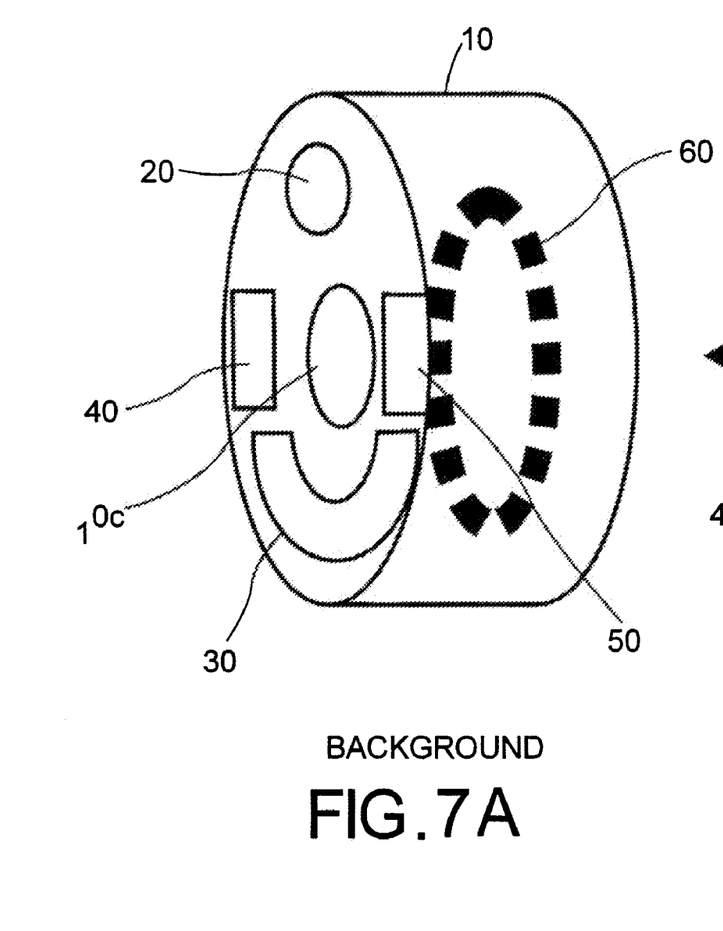
FIG. 7A is a schematic perspective view of a rotation frame configuration provided to explain a background technique of an X-ray CT apparatus.

FIG. 7A is a simplified illustration of the positional relationship between the rotation frame 10 and the bearings 60 illustrated in FIG. 8. As shown in this figure, a plurality of devices, such as, an X-ray tube 20, an X-ray detector 30, a high voltage generation apparatus 40 and a cooling apparatus 50, are mounted on a vertical circle member of the rotation frame 10 in the gantry of the apparatus. The rotation frame 10 is rotatably supported by a fixing base through a plurality of bearing units that are provided between an inner surface of the drum member of the rotation frame 10 and an outer surface of a drum member of the fixing base.

Figure 7B:
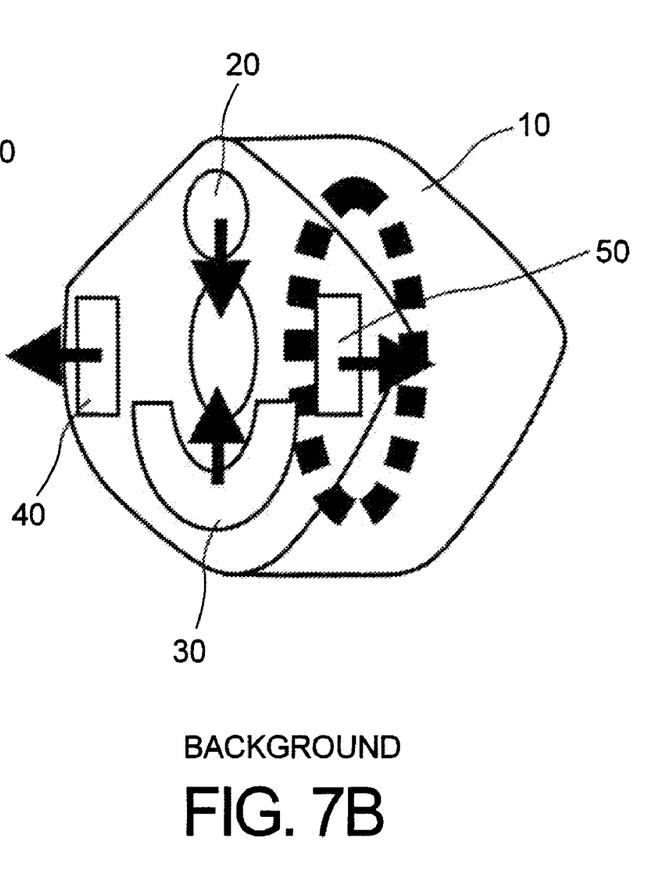
FIG. 7B is a schematic perspective view illustrating rotation distortion of the rotation frame configuration illustrated in FIG. 7A at a high speed rotation.

The rotation frame 10 is usually made of an aluminium (Al) casting. Consequently, when a rotation speed of the rotation frame 10 is increased in order to increase observation efficiencies, distortions of the rotation frame 10 occur due to rotation accelerations that are given in accordance with the weight of the rotation frame 10. For instance, rotation distortions may occur along directions as shown by arrows in FIG. 7B due to high speed rotation. FIG. 7B shows a case where X-ray tube 20 and X-ray detector 30 are slightly displaced so as to shorten a predetermined distance between them due to distortions of the rotation frame 10. Of course, in contrast to the arrows shown in FIG. 7B, it may occur that X-ray tube 20 and X-ray detector 30 are displaced so as to expand the predetermined distance between them as may occur case by case. Such displacements of X-ray tube 20 and X-ray detector 30 due to a high speed rotation of the rotation frame 10 generate errors in the acquired image data through the detector and deteriorate the quality of reproduced images based on incorrect data. It may become a serious problem for an image diagnosis apparatus.

To reduce such distortions due to a high speed rotation of the rotation frame, it has been proposed, for example, as suggested in Japanese Patent Application Publication 8-102550, to provide appropriate weight members on the rotation frame in order to prevent displacements of the rotation frame due to rotation and to maintain balance of the rotation frame. However, such a construction adds weight and makes the apparatus complicated and heavy.

Incidentally, in an actually used X-ray CT imaging apparatus of a high speed rotation, a rotation T for acquiring a necessary projection data of an object by rotating an X-ray source one rotation around an object takes about 0.5 second. Thus, a rotation frame in a high speed imaging X-ray CT apparatus needs to rotate in a high speed of two revolutions during one second.

Generally, supposing that a revolution radius is R (cm), a relationship between the rotation time T and a centrifugal acceleration G is represented by the following equation (1).

$$G = 0.0402(R/T^2) \qquad (1)$$

For example, in a case the revolution radius is be 75 cm, the centrifugal acceleration due to the frame rotation becomes about 12 G. Accordingly, it will be understood that the rotation frame having an X-ray source, an X-ray detector and various apparatus in a high speed X-ray CT imaging apparatus receives a large acceleration during rotation. When a rotation radius R of X-ray source is 75 cm, centrifugal acceleration to the rotation frame during a rotation becomes about 12 G from the formula (1). Thus, in a high speed imaging X-ray CT apparatus, the rotation frame made of aluminium and various devices mounted on the rotation frame, i.e., an X-ray tube, an X-ray detector, a high voltage generator and cooling apparatus, also receive a large centrifugal force during the rotation. Nevertheless, to increase observation efficiencies for instance, it is desired to increase one rotation time of X-ray tube and X-ray detector up to 0.25 second, i.e., 4 rotations per one second. In this case, even when a rotation radius R is 75 cm, the centrifugal acceleration during a high speed rotation becomes about 48 G from the formula (1). If a rotation radius also is increased in order to increase observation efficiency, the centrifugal acceleration is further increased.

To prevent such occurrence of distortions of the rotation frame 10 due to a large centrifugal acceleration, it is considered to strengthen a rigidity of the rotation frame 10 itself by making an iron casting and strengthening a rigidity of the bearings by using large size bearing units. However, since rotation inertia of the rotation frame itself also increases in accordance with the increase of the rigidity of the rotation frame during a high speed rotation, it becomes necessary to strengthen a braking force in order to stop the rotating frame. Consequently, an X-ray CT apparatus becomes much larger and heavier as a whole when measures are taken to strengthen the bearing units and the rotation frame.

As explained above, when a rotation speed of a rotation frame in an X-ray CT apparatus is increased, the rotation frame receives a larger centrifugal force. Nevertheless, it is strongly desired to achieve a much higher speed X-ray CT apparatus having a much larger aperture radius of the rotation frame in order to increase observation efficiency of an X-ray CT apparatus.

SUMMARY OF THE INVENTION

The present invention addresses the problems and defects of the conventional apparatus and provides a new X-ray CT apparatus that can constrain distortions of a rotation frame due to high speed rotation in order to avoid occurrence of displacements of an X-ray source and an X-ray detector that are provided on the rotation frame. Consequently, the X-ray CT apparatus according to the present invention can achieve a high efficiency of diagnosis without increasing the weight of the X-ray CT apparatus.

According to one aspect of the present invention, there is provided an X-ray CT apparatus including a cylindrical rotation frame having an annulus portion extended along a rotation axis and a circular rib portion provided on an inner surface of the annulus portion so as to be substantially perpendicular to the rotation axis as a ring projection; an X-ray source for irradiating X-rays through an object and an X-ray detector provided opposite the X-ray source for acquiring projection data through the object, the X-ray source and the X-ray detector provided on the circular rib portion at opposite positions about the rotation axis; a plurality bearing units provided on an outer surface of the cylindrical rotation frame so as to surround the outer surface of the cylindrical rotation frame in a ring-configuration; and a fixed frame supporting body configured to rotatably support the cylindrical rotation frame through the plurality bearing units.

As thus configured, there is provided a novel X-ray CT apparatus that can achieve high speed rotation of a rotation frame for supporting an X-ray source (X-ray tube) and an X-ray detector while preventing distortions of the rotation frame from occurring during high speed rotation. Thus, the X-ray CT apparatus of the present invention can prevent displacements of the X-ray source and the X-ray detector from occurring during a high speed rotation of the rotation frame. It is also possible for the X-ray CT apparatus of the present invention to increase observation efficiencies while being kept light weight.

According to another aspect of the present invention, there is provided an X-ray CT apparatus including a drum type rotation frame having an annular member extending along a rotation axis and a rib member projected from an inner surface of the annular member so as to be substantially perpendicular to the rotation axis; an X-ray source provided on the rib member for irradiating X-ray beams onto an object and an X-ray detector provided on the rib member opposite the X-ray source about the rotation axis; a plurality of bearing units provided on and surrounding an outer surface of the drum rotation frame in a ring configuration; and a drum fixed frame constructed so as to rotatably support the drum rotation frame through the plurality of bearing units.

According to a further aspect of the present invention, the X-ray CT apparatus includes a rib member provided in a circular configuration on the inner surface of the annular member; and the plurality of bearing units is provided so as to surround the outer surface of the annular member in one ring configuration.

According to another aspect of the present invention each of the plurality of bearing units includes a ball member, a rotation side receiving member fixed on an outer surface of the drum type rotation frame and a fixed side receiving member connected on an inner surface of the fixed frame.

In the X-ray CT apparatus according to another aspect of the present invention, each of the plurality of bearing units includes a ball member, a rotation side receiving member fixed on an outer surface of the drum type rotation frame and a fixed side receiving member connected on an inner surface of the fixed frame, wherein the ball member contacts at two points to the rotation side receiving member and the fixed side receiving member, respectively.

In the X-ray CT apparatus according to another aspect of the present invention, each of the plurality of bearings unit includes a four point contacting bearing a wherein a ball member contacts each of a rotation side receiving member fixed on an outer surface of the drum type rotation frame and a fixed side receiving member connected on an inner surface of the fixed frame at four points on two hypothetical lines at an angle of plus (+) 45 degrees and an angle of minus (−) 45 degrees from a horizontal line parallel to the rotation axis.

In the X-ray CT apparatus according to another aspect of the present invention, each of the plurality of bearings unit includes two angular contact bearings that are arranged in a parallel; one ball member of the two angular contact bearings contacts each of a rotation side receiving member and a fixed side receiving member at an angle of plus (+) 45 degrees from a hypothetical vertical line, and the other ball member contacts each of a rotation side receiving member and a fixed side receiving member at an angle of minus (−) 45 degrees from the hypothetical vertical line.

In the X-ray CT apparatus according to another aspect of the present invention, a plurality of bearings units of at least two ring-like configuration are interposed between the outer surface of the drum type rotation frame and the inner surface of the drum type fixed frame separated from a center line of the rib member.

In the X-ray CT apparatus according to a further aspect of the present invention, a plurality of bearing units of three ring-like configurations are interposed between the outer surface of the drum type rotation frame and the inner surface of the drum type fixed frame, wherein one ring of the plurality of bearing units is provided on a center line of the rib member and the other two rings of the plurality of bearings units are respectively provided at separated positions from the center line of the rib member.

In the X-ray CT apparatus according to a further aspect of the present invention, a plurality of bearing units of at least two ring configurations are provided on the outer surface of the drum type rotation frame at symmetrical positions with respect to a center line of the rib member.

In the X-ray CT apparatus according to a further aspect of the present invention, a plurality of bearing units of at least two ring configurations are provided on the outer surface of the drum type rotation frame at asymmetrical positions with respect to a center line of the rib member.

The X-ray CT apparatus according to a further aspect of the present invention, further includes a tilting mechanism configured to tilt the rotation axis of the rotation frame in a predetermined range of angles.

According to a further aspect of the present invention, there is provided an X-ray CT apparatus including a drum type rotation frame having an annular member having a predetermined length along a rotation axis; an X-ray source and an X-ray detector provided on an inner surface of the annular member opposite each other about the rotation axis; a plurality of bearing units surrounding an outer surface of the drum type rotation frame in a ring-like configuration; and a drum type fixed frame configured to rotatably support the drum type rotation frame through the plurality of bearing units.

According to a further aspect of the X-ray CT apparatus of the present invention, even when a rotation frame receives a large centrifugal acceleration during a high speed rotation, the rigidity of the fixed frame and the plurality of bearing units provided between the fixed frame and the rotation frame can prevent the rotation frame from expanding to outer sides.

Accordingly, it becomes possible to prevent an X-ray tube and an X-ray detector on the rotation frame from displacing at predetermined positions. Consequently, deterioration of reconstructed images can be prevented.

According to a further aspect of the X-ray CT apparatus of the present invention, even when the rotation frame is rotated at a higher speed and the rotation frame receives much larger centrifugal accelerations, pitching vibrations of the rotation frame can be prevented from occurring, since the rigidities along a forward and backward directions of the rotation frame are increased. Consequently, occurrences of displacements of relative positions of the X-ray tube and the X-ray detector can be reduced when the rotation frame rotates in a high speed. Thus, deterioration of reconstructed images can be prevented.

According to a further aspect of the X-ray CT apparatus of the present invention, tilting imaging operations can be performed by tilting the rotation frame supporting unit at various angles in a predetermined range of angles while maintaining a rotation center of the rotation frame.

BRIEF DESCRIPTION OF THE DRAWINGS

The accompanying drawings, which are incorporated in and constitute part of this specification, illustrate various embodiments and/or features of the present invention, and together with the description, serve to explain the present invention. Where possible, the same reference number will be used throughout the drawings to describe the same or like parts. In the drawings.

DESCRIPTION OF THE PREFERRED EMBODIMENTS

Referring now to FIGS. 1-8, embodiments of the present invention will be explained. As an exemplary embodiment according to the present invention, a helical scan X-ray CT apparatus will be described. Of course, the present invention is applicable to any type of X-ray CT apparatus.

Figure 1:
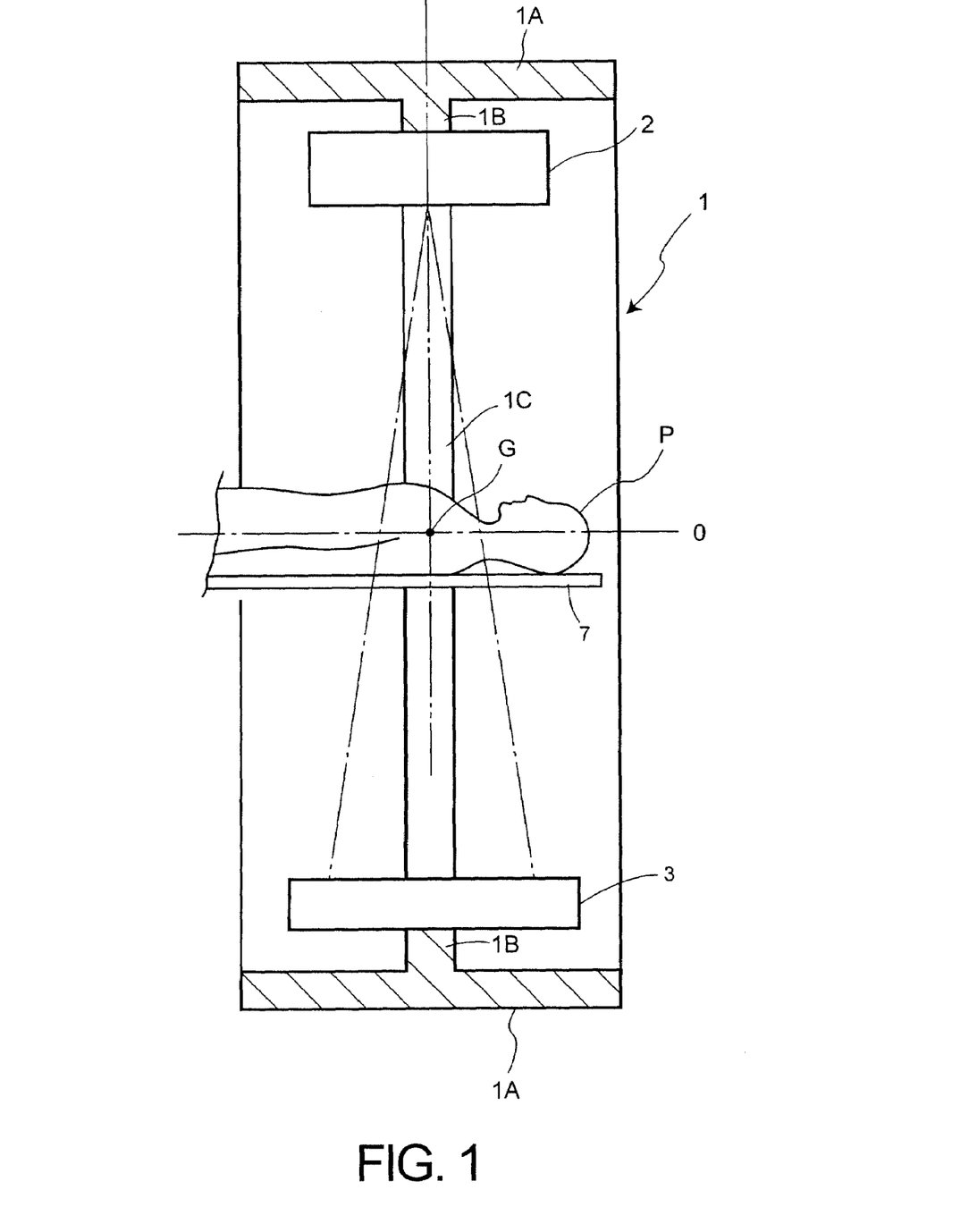
FIG. 1 is a schematic cross-sectional view of a drum type rotation frame applicable to an X-ray CT apparatus consistent with the present invention.

FIG. 1 is a cross-section view of a drum type rotation frame of an X-ray CT apparatus consistent with the present invention. As shown in FIG. 1, a drum type rotation frame 1 includes an annulus ring member 1A surrounding a rotation axis 0 of the drum type rotation frame 1 and a circular rib member 1B that is projected from an inner surface of the annulus ring member 1A along a hypothetical line Y that orthogonally crosses the rotation axis O at a substantial center of the annulus ring member 1A and passes through a center of gravity G of the rotation frame. For instance, the annulus ring member 1A and the circular rib member 1B are made as a unitary body by an aluminium (Al) casting. Of course, it is possible to make the unitary body by an iron (Fe) casting. An X-ray tube 2 is provided on the rib member 1B projected from the annulus ring member 1A at a prescribed position. An X-ray detector 3 is provided opposite the rib member 1B facing the X-ray tube 2 about the rotation axis O. X-ray tube 2 irradiates fan beams over an object P so as to pass a center of gravity G of the rotation frame and X-ray detector 3 detects penetrated X-rays. A center portion of the circular rib member 1B forms an aperture 1C through which the rotation center axis O passes. When an object P supported on a top plate 7 is moved into the aperture 1C, the drum type rotation frame 1 rotates on the rotation axis O so as to irradiate X-ray beams through the object P in various directions in order to detect various projection data through X-ray detector. As shown in FIG. 1, the center line Y of the rib member 1B projected from an inner surface of the annulus ring member 1A orthogonally crosses the rotation axis O and passes through the center of gravity of the rotation frame 1.

In the embodiment illustrated in FIG. 1, the annulus ring member 1A of the drum type rotation frame 1 and the circular rib member 1B projected from an inner surface of the annulus ring member 1A have a unitary body. Of course, it is possible to make the rib member 1B as a plurality of projection members arranged on the inner surface of the annulus ring member 1A. Further, it is also possible to directly provide X-ray tube 2 and X-ray detector 3 on the inner surface of the drum type rotation frame 1A so as to face opposite each other in order to make a larger aperture 1C in the absence of the projected rib member 1B.

Figure 2:
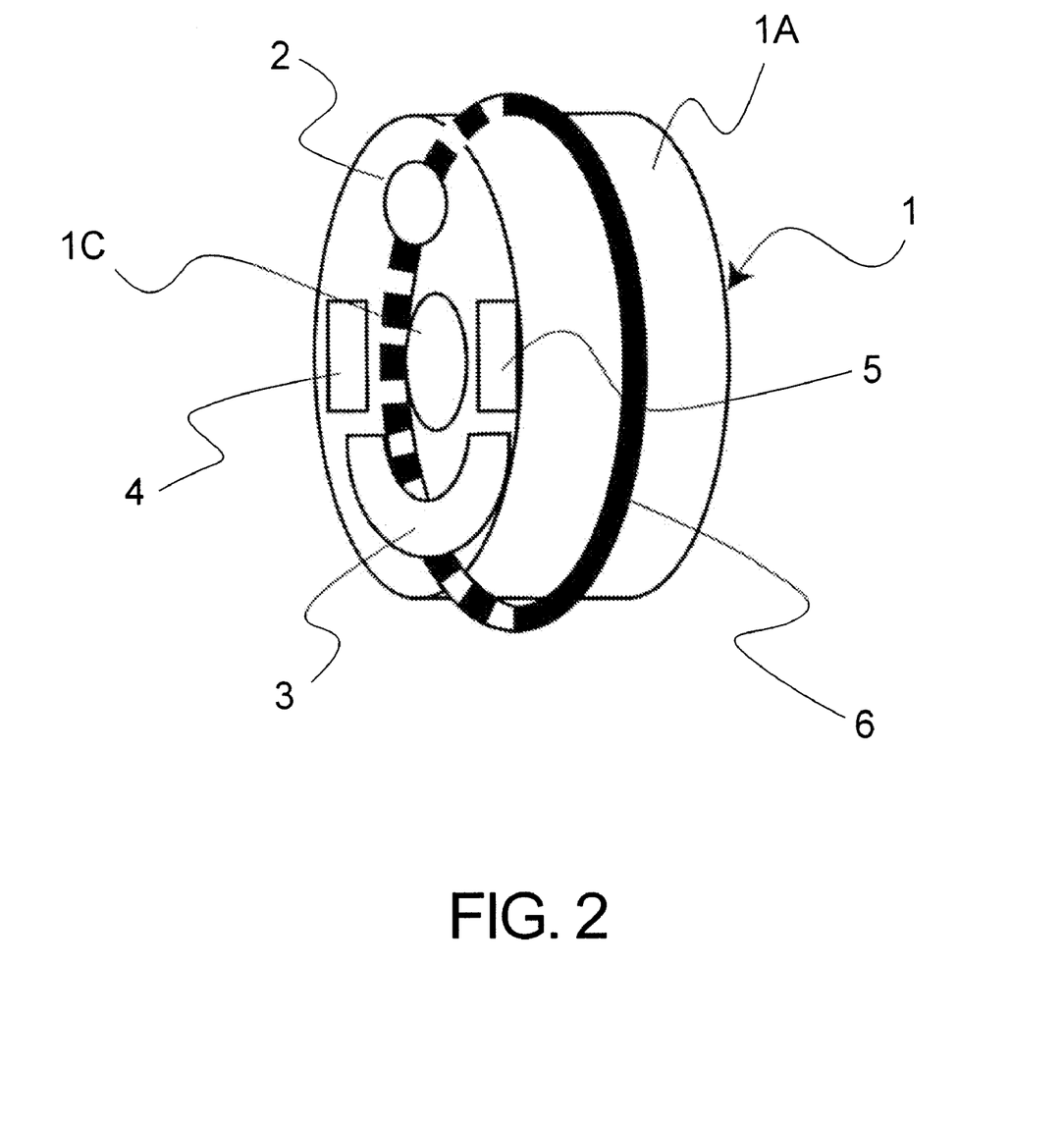
FIG. 2 is a schematic perspective view of the drum type rotation frame applicable to an X-ray CT apparatus consistent with the present invention in order to illustrate relationships between the rotation frame and a plurality of bearings unit surrounding the outer surface of the rotation frame in a ring like configuration.

FIG. 2 shows a simplified construction of the drum type rotation frame 1 illustrated in FIG. 1. As shown in FIG. 2, in the rotation frame 1 applicable to an X-ray CT apparatus according to the present invention, a plurality of bearing units 6 is provided at positions corresponding to the projected member 1B on an outer surface of the annulus ring member 1A in a ring-like configuration so as to surround the outer surface of the annulus ring member 1A. Thus, the entire body of the drum type rotation frame 1 is rotatably supported as a rotation shaft by a fixed frame through the plurality of bearing units 6 arranged in a ring-like configuration. In the rotation frame 1, an X-ray tube 2, an X-ray detector 3, a high voltage generation apparatus 4 and other units, such as a data acquisition apparatus, a cooling apparatus and balancing weights are fixed at respective prescribed positions. As the entire body of a rotation shaft is surrounded by the plurality of bearings unit 6, an outer surface of the rotation frame 1 is rotatably supported by a fixed frame. Consequently, both rigidities of the plurality of bearing units 6 and of the fixed frame can constrain distortions of the rotation frame 1 during high speed rotation.

Figure 3:
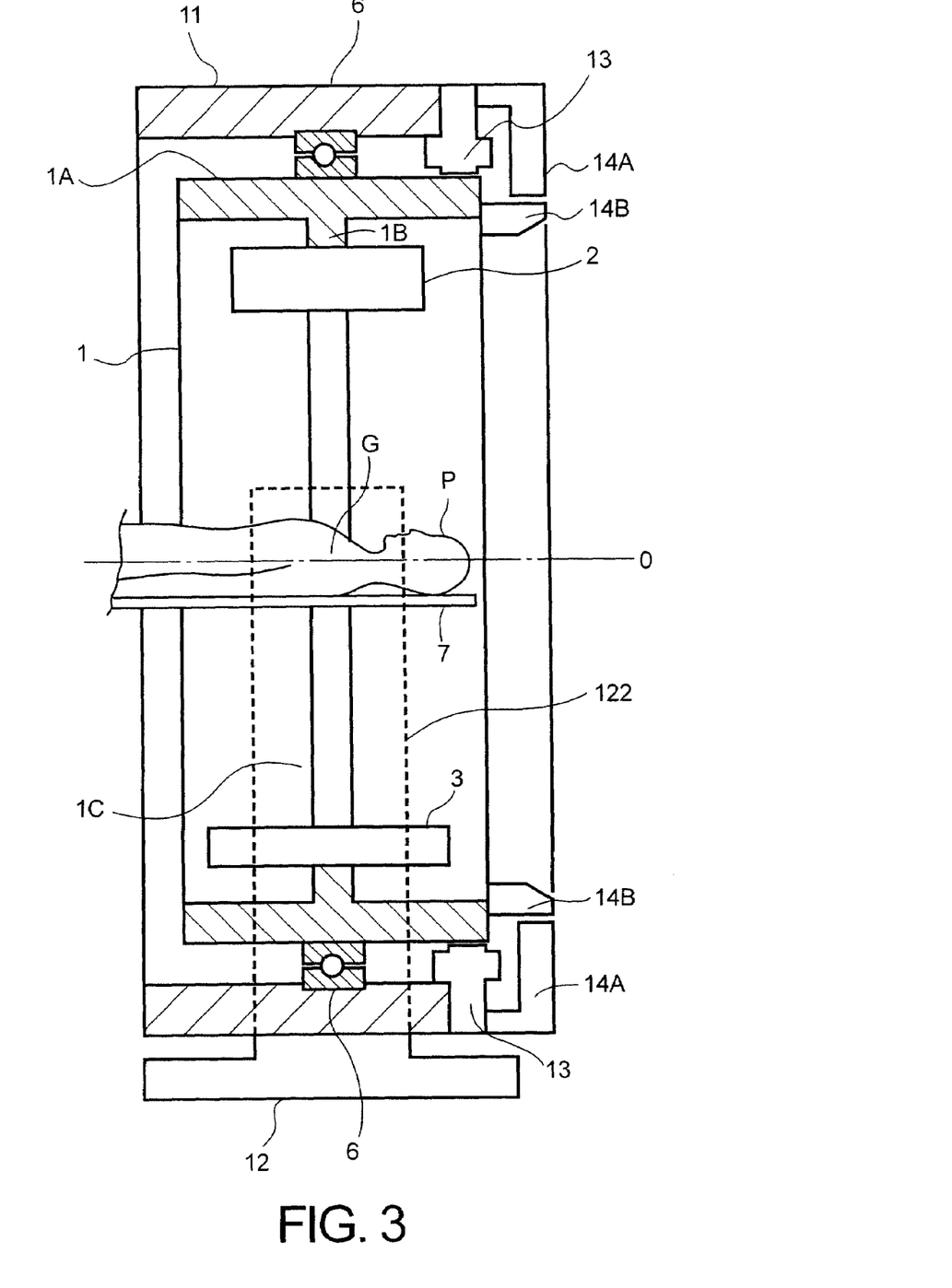
FIG. 3 is a schematic cross-sectional view of an embodiment of a supporting configuration of the rotation frame for the X-ray CT apparatus illustrated in FIG. 1.

FIG. 3 illustrates in more detail an embodiment of a supporting configuration of the drum type rotation frame 1 shown in FIG. 1. A circular fixed frame 11 is coaxially provided on an outer surface of the rotation frame annulus ring member 1A and an outer surface of the annulus ring member 1A of the rotation frame 1 and an inner surface of the circular fixed frame 11 are rotatably supported through a plurality of bearing units 6 arranged in a ring-like configuration. In this embodiment, a plurality of bearing units 6 is provided on the outer surface of the annulus ring member 1A of the rotation frame at substantially equal distances with respect to each other so as to form a ring-like configuration. An outer surface of the circular fixed frame 11 is supported by a gantry stand 12 that is fixed on a floor.

The fixed frame 11 has a rotation axis coaxial to the rotation axis with the drum type rotation frame 1. On one edge portion of the fixed frame 11 are provided a motor 13 configured to rotate the drum type rotation frame 1, a power supply configured to supply power to X-ray tube, X-ray detector and other various devices mounted on the rotation frame 1 and a fixing side data transmission member 14A configured to perform data transmission and reception operations between a control unit (not shown). Facing the fixing side data transmission member 14A, a rotation side data transmission member 14B for transmitting and receiving data is provided on one edge portion of the rotation frame 1. The fixing side data transmission member 14A and the rotation side data transmission member 14B are constructed in a ring-like configuration, respectively. Usually, the power supply to the rotating devices on the rotation frame is performed through a slip ring. The data transmission to and from the fixing side data transmission member 14A and the rotation side data transmission member 14B is performed optically by means of light transmission.

Figure 4A:
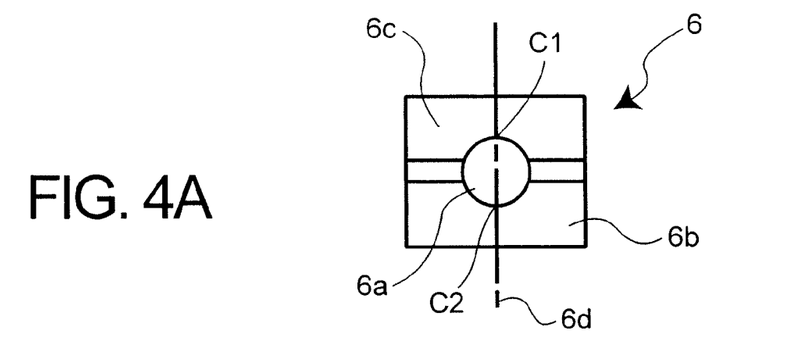
FIG. 4A is a cross-sectional view of an example of two-point contacting type bearings inserted in the rotation frame supporting configuration illustrated in FIG. 3.

Various types of bearings are used as the plurality of bearing units 6. FIG. 4A shows a first construction of the bearings. As shown in FIG. 4A, the bearings 6 includes a ball member 6a (e.g., an iron ball), a rotation side receiving member 6b fixed on an outer surface of the drum type rotation frame 1 and a fixed side receiving member 6c connected on an inner surface of the fixed frame 11. The ball member 6a contacts at two contacting points C1 and C2 to the rotation side receiving member 6b and the fixed side receiving member 6c, respectively. Thus, while centrifugal accelerations are added to the rotation frame 1 along directions orthogonally crossing the rotation axis O when the rotation frame 1 rotates on a center of gravity G at high speed, distortions of the rotation frame 1 can be constrained by the rigidity of the plurality of bearing units 6 and the rigidity of fixed frame 11.

Figure 4B:
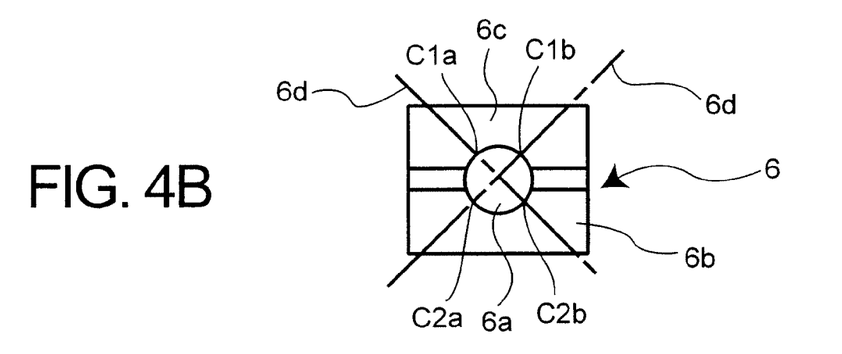
FIG. 4B is a cross-sectional view of an example of four-point contacting type bearings inserted in the rotation frame supporting configuration illustrated in FIG. 3.

FIG. 4B illustrates a four point contacting bearing 6. As shown in FIG. 4B, a ball member 6a contacts each of the rotation side receiving member 6b fixed on an outer surface of the drum type rotation frame 1 and a fixed side receiving member 6c connected on an inner surface of the fixed frame 11 at four points c1a, c1b, c2a and c2b on two hypothetical lines d1, one having an angle of plus (+) 45 degrees and the other having an angle of minus (−) 45 degrees from a horizontal line parallel to the rotation axis. Since rolling resistances of the ball member are dispersed at four contact points, the centrifugal accelerations added to the rotation frame during high speed rotation are also dispersed and transferred to the fixed frame. Thus the rigidity for preventing the rotation frame body from distorting can be increased.

Figure 4C:
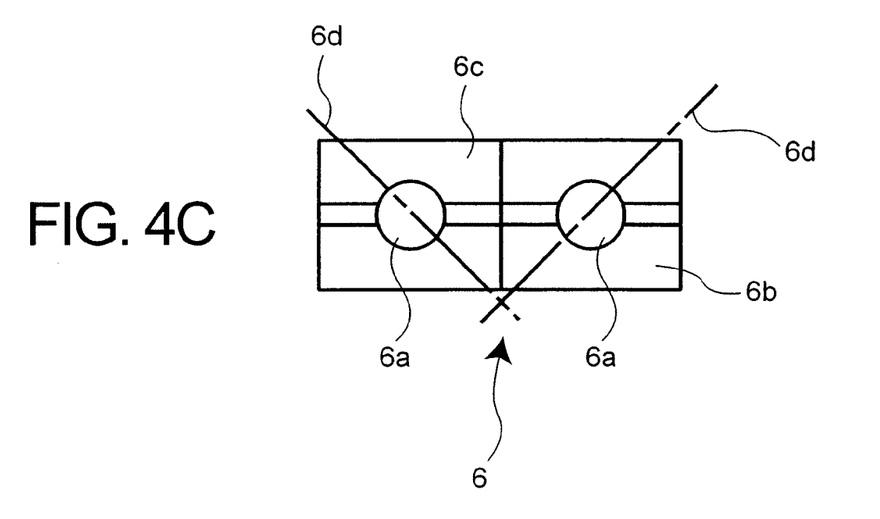
FIG. 4C is a cross-sectional view of an example of two-line angular contact bearings inserted in the rotation frame supporting configuration illustrated in FIG. 3.

FIG. 4C illustrates two angular contact bearings arranged in a parallel. One ball member 6a1 contacts each of a rotation side receiving member and a fixed side receiving member at a first slanted angle, for example, an angle of plus (+) 45 degrees from a hypothetical vertical line in FIG. 4A. The other ball member 6a2 contacts each of a rotation side receiving member and a fixed side receiving member at a second slanted angle, for example, an angle of minus (−) 45 degrees from the hypothetical vertical line. With two angular contact bearings, as explained in FIG. 4B, centrifugal accelerations given to a rotation frame during high speed rotation are also transmitted to the fixed frame upon dispersing through the two angular contact bearings. Accordingly, the structure for preventing a rotation frame from distorting can be strengthened. Thus, it becomes possible to realize a higher speed rotation of the rotation frame of an X-ray CT apparatus.

As explained above, in an X-ray CT apparatus according to the present invention, the entire body of the rotation frame 1 acts as a rotation shaft and an outer surface of the rotation shaft is surrounded by a fixed frame 11 through a plurality of bearing units arranged in a ring configuration surrounding the outer surface of the drum type rotation frame. Consequently, even when the rotation frame 1 receives a large centrifugal acceleration during a high speed rotation, outer expansion of the rotation frame 1 due to the rigidity of the plurality of bearing units and of the fixed frame. Since displacements of the X-ray tube 2 and X-ray detector 3 due to the centrifugal acceleration can be constrained, deterioration of the quality of CT images can be prevented.

Figure 5:
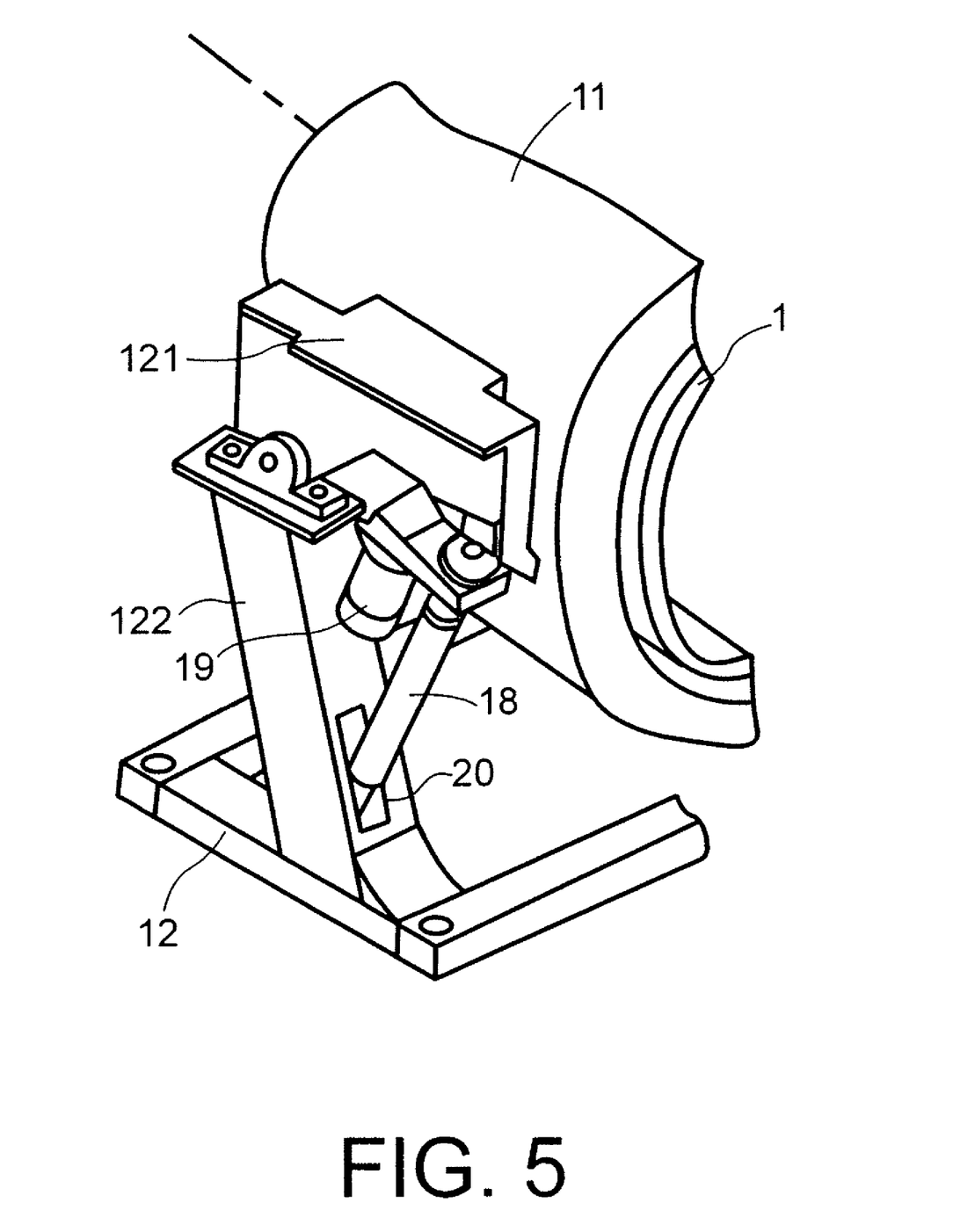
FIG. 5 is a partially cut perspective view of a tilting mechanism for the rotation frame supporting configuration applicable to an X-ray CT apparatus according to the present invention, wherein a rotation axis is maintained.

It also possible to support both the drum type rotation frame and the drum type fixed frame by a tilting mechanism in order to tilt the rotation axis at a prescribed angle from a horizontal axis of the apparatus while maintaining the rotation center. FIG. 5 illustrates one embodiment of the tilting mechanism. The fixed frame 11 is supported by a tilt moving frame 121 that is tilted by an expansion and a contraction of a power cylinder 18. Thus, the rotation frame 1 and the fixed frame can be tilted as a whole in order to vary incidence angles of X-ray beams onto an object. It then becomes possible to acquire projection data from multi-angles of X-ray beams at a higher speed rotation of the rotation frame 1.

In the embodiment shown in FIG. 3, the annulus ring member 1A of the drum type rotation frame 1 and a circular rib member 1B projected on an inner surface of the annulus ring member are formed as a unitary body. Of course, as explained in the embodiment of FIG. 1, it is possible to provide the X-ray tube and the X-ray detector directly on the inner surface of the drum type rotation frame 1 so as to face opposite each other without providing the circular rib member 1B.

Figure 6:
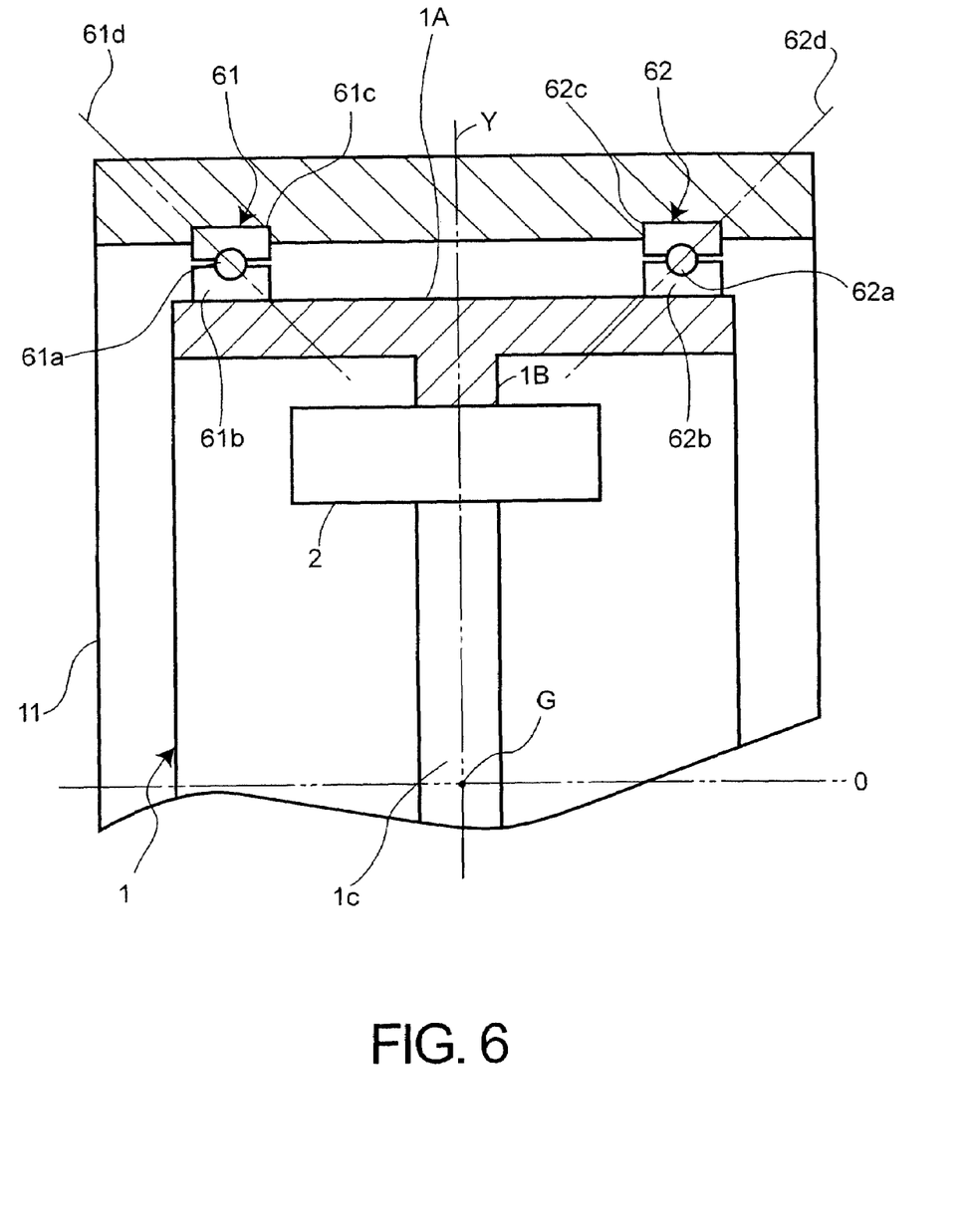
FIG. 6 is a partially cut cross-sectional view of a rotation frame supporting configuration applicable to an X-ray CT apparatus of an another embodiment of the present invention.

FIG. 6 shows another embodiment of X-ray CT apparatus according to the present invention. To avoid repetitious explanation, the same or similar portions of the elements shown in the previous embodiment are identified by the same reference number.

In FIG. 6, a first plurality of bearing units 61 and a second plurality of bearing units 62 are provided between an inner surface of the drum type fixed frame 11 and an outer surface of the drum type rotation frame 1 so as to form two ring-like configurations. The plurality of bearing units of two ring configurations are provided on the outer surface of the drum type rotation frame at symmetrical positions with respect to a center line of the rib member. It is possible to provide the plurality of bearing units of two ring configurations on the outer surface of the drum type rotation frame at unsymmetrical positions with respect to a center line of the rib member. Further, it is possible to provide a plurality of bearing units of three ring-like configurations interposed between the outer surface of the drum type rotation frame and the inner surface of the drum type fixed frame. For instance, one ring of the plurality of bearing units can be provided on a center line of the rib member and other two rings of the plurality of bearings units can be respectively provided at separated positions from the center line of the rib member.

In the embodiment shown in FIG. 6, a first bearing unit 61 and a second bearing unit 2 are respectively used by dividing the two angular contact bearings 61 and 62, such as shown in FIG. 4C, into a right side unit and a left side unit. Thus, a first hypothetical line 61d of the bearing unit 61 connected through a center of the ball 61a in the first bearing unit 61 at an angle of minus (−) 45 degrees and a second hypothetical line 62d of the bearing unit 62 connected through a center of the ball 62d in the second bearing unit 62 at an angle of plus (+) 45 degrees cross in the inside of the drum type rotation frame 1.

According to this embodiment, it becomes possible to powerfully constrain expansions of the rotation frame 1 due to large centrifugal acceleration during high speed rotation by both rigidity of the fixed frame 11 and rigidity of a first and a second bearing units 61 and 62 provided between the fixed frame 11 and the rotation frame 1. Further, rigidity along back and forward directions of rotation frame 1 is increased by using the two angular contact bearings as the first and second bearing units 61 and 62. Thus, pitching movements of the rotation frame 1 can be reduced. Consequently, displacements in the relative positions of the X-ray tube 2 and X-ray detector 3 can be prevented from occurring during high speed rotation and deteriorations of reconstructed images can be prevented from occurring.

In the embodiment illustrated in FIG. 6, two angular contact bearings are used as the two ring-like arrangements of bearing units 61 and 62. It is also possible to use the bearings unit such as shown in FIGS. 4A or 4B.

In the embodiment illustrated in FIG. 6, two ring-like arrangements of bearing units 61 and 62 are symmetrically located about a hypothetical line Y that is orthogonally crossing the rotation axis O of the rotation frame 1 so as to pass through a center of gravity G of the rotation frame 1. Of course, it is possible to locate the two rings of the bearings units 61 and 62 at asymmetrical positions about the hypothetical line Y. In this case, the effects of the present invention can be obtained.

In the embodiment illustrated in FIG. 6, as shown in FIG. 3, the fixed frame 11 mounts a motor for rotating the rotation frame 1, a power supplying unit and a data transmission unit for transmitting and receiving to and from a control unit. Further, as illustrated in FIG. 5, it is possible to install a tilting mechanism for tilting the fixed frame 11 in a predetermined angular range.

In the embodiment illustrated in FIG. 6, the drum type rotation frame 1 includes of an annulus ring member 1A and a circular rib member 1B projecting from an inner surface of the annulus ring member 1A in a unitary form. Of course, as explained in the embodiment illustrated in FIG. 1, it is possible to directly provide an X-ray tube 2 and an X-ray detector 3 on an inner surface of the annulus ring member 1A without providing the circular rib member 1B, therein to increase the size of the aperture 1C.

In the above-explained embodiments, the bearing materials 61 and 62 are formed on the outer surface of the annulus ring portion 1b of the rotating body 1 in two rows with a separating distance. Of course, it is possible to form the bearing materials in three or more rows.

Other embodiments consistent with the present invention will be apparent to those skilled in the art from consideration of the specification and practice of the present invention disclosed herein. It is intended that the specification and examples be considered as exemplary only, with a true scope and spirit of the present invention being indicated by the following claims.

The invention claimed is:

1. An X-ray CT apparatus comprising:
   a drum type rotation frame including an annular member extending along a rotation axis and a rib member projected from an inner surface of the annular member so as to be substantially perpendicular to the rotation axis;
   an X-ray source, supportably coupled to the rib member, for irradiating X-ray beams onto an object and an X-ray detector provided on the rib member opposite the X-ray source about the rotation axis so as to face the X-ray source, the X-ray source being disposed between the rotation axis and the rib member;
   a bearing unit surrounding an outer surface of the drum type rotation frame in a ring-like configuration; and
   a drum type fixed frame configured to rotatably support the drum type rotation frame through the bearing unit.

2. The X-ray CT apparatus according to claim 1, wherein the rib member is provided in a circular configuration on the inner surface of the annular member; and
   the bearing unit is provided so as to surround the outer surface of the annular member in a one ring-like configuration.

3. The X-ray CT apparatus according to claim 1, wherein the annular member and the rib member are constructed as a unitary body.

4. The X-ray CT apparatus according to claim 1, wherein the bearing unit is interposed between the outer surface of the annular member and the inner surface of the drum type fixed frame so as to orthogonally cross the rotation axis of the rotation frame.

5. The X-ray CT apparatus according to claim 1, wherein the fixed frame is coaxially provided on an outer surface of the drum type rotation frame so as to rotatably support the rotation frame through a plurality of bearing units arranged in one ring-like configurations on the outer surface of the rotation frame.

6. The X-ray CT apparatus according to claim 1, wherein the bearing unit includes a ball member, a rotation side receiving member fixed on an outer surface of the drum type rotation frame and a fixed side receiving member connected on an inner surface of the fixed frame, and the ball member contacts at two points to the rotation side receiving member and the fixed side receiving member, respectively.

7. The X-ray CT apparatus according to claim 1, wherein the bearing unit includes a ball member, a rotation side receiving member fixed on an outer surface of the drum type rotation frame and a fixed side receiving member connected on an inner surface of the fixed frame.

8. The X-ray CT apparatus according to claim 1, wherein the bearing unit comprises a four point contacting bearing having a ball member contacting each of a rotation side receiving member fixed on an outer surface of the drum type rotation frame and a fixed side receiving member connected on an inner surface of the fixed frame at four points on two hypothetical lines of different slanted angles from a horizontal line parallel to the rotation axis, respectively.

9. The X-ray CT apparatus according to claim 1, wherein the bearing unit comprises two angular contact bearings arranged in a parallel and each having a ball member, wherein one ball member contacts each of a rotation side receiving member and a fixed side receiving member at an angle of plus (+) 45 degrees from a hypothetical vertical line and the other ball member contacts each of a rotation side receiving member and a fixed side receiving member at an angle of minus (−) 45 degrees from the hypothetical vertical line.

10. The X-ray CT apparatus according to claim 1, further comprising:
a plurality of bearing units that include bearing units of at least two ring-like configurations interposed between the outer surface of the drum type rotation frame and the inner surface of the drum type fixed frame separated from a center line of the rib member.

11. The X-ray CT apparatus according to claim 1, further comprising:
a plurality of bearing units that include bearing units of three ring-like configurations interposed between the outer surface of the drum type rotation frame and the inner surface of the drum type fixed frame, one ring of the plurality of bearing units is provided on a center line of the rib member and the other two rings of the plurality of bearings units are respectively provided at separated positions from the center line of the rib member.

12. The X-ray CT apparatus according to claim 1, further comprising:
a plurality of bearing units that include bearing units of at least two ring configurations provided on the outer surface of the drum type rotation frame at symmetrical positions with respect to a center line of the rib member.

13. The X-ray CT apparatus according to claim 1, further comprising:
a plurality of bearing units that include bearing units of at least two ring configurations provided on the outer surface of the drum type rotation frame at asymmetrical positions with respect to a center line of the rib member.

14. The X-ray CT apparatus according to claim 1, further comprising:
a plurality of bearing units that include bearing units of at least two ring configurations provided on respective edge portions of the outer surface of the drum type rotation frame.

15. The X-ray CT apparatus according to claim 1, further comprising a tilting mechanism configured to tilt the rotation axis of the rotation frame through a predetermined range of angles.

16. An X-ray CT apparatus comprising:
a drum type rotation frame including an annular member having a predetermined length along a rotation axis and a rib member projected from an inner surface of the annular member so as to be substantially perpendicular to the rotation axis;
an X-ray source and an X-ray detector provided opposite each other on the rib member projected from the inner surface of the annular member so as to face each about the rotation axis, the X-ray source and the X-ray detector each being disposed between the rotation axis and the rib member;
a plurality of bearing units surrounding an outer surface of the drum type rotation frame in a ring-like configuration; and
a drum type fixed frame configured to rotatably support the drum type rotation frame through the plurality of bearing units.

17. The X-ray CT apparatus according to claim 16, wherein each of the plurality of bearing units includes a ball member, a rotation side receiving member fixed on an outer surface of the drum type rotation frame and a fixed side receiving member connected on an inner surface of the fixed frame.

18. The X-ray CT apparatus according to claim 16, wherein each of the plurality of bearings unit comprises two angular contact bearings having respective ball members and arranged in a parallel; wherein one ball member of the two angular contact bearings contacts each of a rotation side receiving member and a fixed side receiving member at an angle of plus (+) 45 degrees from a hypothetical vertical line, and the other ball member contacts each of a rotation side receiving member and a fixed side receiving member at an angle of minus (−) 45 degrees from the hypothetical vertical line.

19. The X-ray CT apparatus according to claim 16, wherein the plurality of bearing units comprises bearing units of at least two ring-like configurations provided at positions separated from a hypothetical center line orthogonally crossing the rotation axis of the rib member and passing through a center of gravity of the rotation frame.

20. The X-ray CT apparatus according to claim 16, wherein the plurality of bearing units comprises bearing units of three ring-like configuration interposed between the outer surface of the drum type rotation frame and the inner surface of the drum type fixed frame, one ring of the plurality of bearing units provided on a hypothetical center line orthogonally crossing the rotation axis of the rib member and passing through a center of gravity of the rotation frame and other two rings of the plurality of bearings units respectively provided at separated positions from the hypothetical center line.

21. The X-ray CT apparatus according to claim 16, wherein the plurality of bearing units comprises bearing units of at least two ring configurations provided on the outer surface of the drum type rotation frame at symmetrical positions with respect to a center line of the rib member.

22. The X-ray CT apparatus according to claim 16, wherein the plurality of bearing units comprise bearing units of at least two ring configurations provided on the outer surface of the drum type rotation frame at asymmetrical positions with respect to a center line of the rib member.

23. The X-ray CT apparatus according to claim 16, wherein the plurality of bearing units comprises bearing units of at least two ring configurations provided on respective edge portions of the outer surface of the drum type rotation frame.

24. The X-ray CT apparatus according to claim 16, further comprising a tilting mechanism configured to tilt the rotation axis of the drum type rotation frame through a prescribed range of angles.

* * * * *